US010667257B2

(12) United States Patent
Van den Dungen

(10) Patent No.: US 10,667,257 B2
(45) Date of Patent: May 26, 2020

(54) REMOTE INITIATION OF TASKS ON IDLE WIRELESS COMPUTING DEVICES

(71) Applicant: KONINKLIJKE PHILIPS N.V., Eindhoven (NL)

(72) Inventor: Wilhelmus Andreas Marinus Arnoldus Maria Van den Dungen, Boxtel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 147 days.

(21) Appl. No.: 15/763,536

(22) PCT Filed: Sep. 29, 2016

(86) PCT No.: PCT/EP2016/073163
§ 371 (c)(1),
(2) Date: Mar. 27, 2018

(87) PCT Pub. No.: WO2017/055382
PCT Pub. Date: Apr. 6, 2017

(65) Prior Publication Data
US 2018/0270813 A1  Sep. 20, 2018

(30) Foreign Application Priority Data
Sep. 29, 2015 (EP) .................................... 15187384

(51) Int. Cl.
*H04W 72/04* (2009.01)
*H04W 52/02* (2009.01)
(Continued)

(52) U.S. Cl.
CPC ....... *H04W 72/0446* (2013.01); *A61B 5/0022* (2013.01); *A61B 5/747* (2013.01);
(Continued)

(58) Field of Classification Search
CPC ....... A61B 5/0022; A61B 5/747; H04L 67/12; H04W 4/38; H04W 52/0219;
(Continued)

(56) References Cited

U.S. PATENT DOCUMENTS

| 8,565,109 B1 | 10/2013 | Poovendran et al. |
| 2006/0046714 A1* | 3/2006 | Kalavade ............... H04M 3/54 455/428 |

(Continued)

FOREIGN PATENT DOCUMENTS

| EP | 2866501 A1 | 4/2015 |
| JP | H0478233 A | 3/1992 |

*Primary Examiner* — Kashif Siddiqui

(57) ABSTRACT

In various embodiments, a wireless computing device (102, 202, 302) for monitoring a person (100) may include: a processor (230); one or more sensors (236) operably coupled with the processor; and one or more radio antennas (232) operably coupled with the processor. The processor may be configured to transition the wireless computing device between at least an idle state and an active state, and to receive, from a remote computing device (112, 212, 312) via the one or more radio antennas while the wireless computing device is in the idle state, via control plane signaling, a request for one or more data points pertaining to a context of the person. One or more sensor signals may then be obtained from the one or more sensors. The requested one or more data points may be generated based on the one or more sensor signals and provided to the remote computing device via the one or more radio antennas.

13 Claims, 4 Drawing Sheets

(51) Int. Cl.
    *H04W 4/38*   (2018.01)
    *A61B 5/00*   (2006.01)
    *H04L 29/08*  (2006.01)
    *H04W 72/10*  (2009.01)
    *H04W 84/22*  (2009.01)
(52) U.S. Cl.
    CPC .............. *H04L 67/12* (2013.01); *H04W 4/38*
        (2018.02); *H04W 52/0219* (2013.01); *H04W
        52/0229* (2013.01); *H04W 72/10* (2013.01);
        *H04W 84/22* (2013.01); *Y02D 70/00*
        (2018.01); *Y02D 70/1242* (2018.01); *Y02D
        70/1262* (2018.01); *Y02D 70/142* (2018.01);
        *Y02D 70/144* (2018.01); *Y02D 70/164*
        (2018.01); *Y02D 70/26* (2018.01)
(58) Field of Classification Search
    CPC ......... H04W 52/0229; H04W 72/0446; H04W
        72/10; H04W 84/22; Y02D 70/00; Y02D
        70/1242; Y02D 70/1262; Y02D 70/142;
        Y02D 70/144; Y02D 70/164; Y02D 70/26
    See application file for complete search history.

(56) References Cited

U.S. PATENT DOCUMENTS

| | | | |
|---|---|---|---|
| 2006/0171368 A1* | 8/2006 | Moinzadeh | H04W 68/00 370/346 |
| 2011/0230171 A1 | 9/2011 | Kasper | |
| 2011/0288379 A1* | 11/2011 | Wu | A61B 5/02 600/301 |
| 2013/0065569 A1 | 3/2013 | Leipzig et al. | |
| 2014/0228062 A1 | 8/2014 | Rubowitz | |
| 2015/0116127 A1* | 4/2015 | Lynch | H04W 52/0229 340/870.02 |
| 2015/0201454 A1* | 7/2015 | Shukair | H04W 76/25 370/329 |

* cited by examiner

REMOTE INITIATION OF TASKS ON IDLE WIRELESS COMPUTING DEVICES

CROSS-REFERENCE TO PRIOR APPLICATIONS

This application is the U.S. National Phase application under 35 U.S.C. § 371 of International Application No. PCT/EP2016/073163, filed on Sep. 29, 2016, which claims the benefit of European Patent Application No. 15187384.1, filed on Sep. 29, 2015. These applications are hereby incorporated by reference in their entirety herein.

FIELD OF THE INVENTION

The present invention is directed generally to wireless communications. More particularly, various inventive methods and apparatus disclosed herein relate to remotely initiating tasks on idle wireless computing devices such as user equipment.

BACKGROUND OF THE INVENTION

Various wireless computing devices (e.g., "user equipment" in the telecommunications context) may be equipped with a variety of sensors that enable the devices to be used to remotely monitor various attributes of persons-of-interest (e.g., at-risk patients, the elderly, children, inmates, etc.) in various ways. For example, personal emergency response systems ("PERS") may be carried by at-risk patients (e.g., the elderly) to enable them to reach out to medical personnel, and/or to be monitored by medical personnel, at all times. However, maintaining a network connection between a wireless computing device carried by a person-of-interest and a remote computing device operated by someone in charge of monitoring the person-of-interest (e.g., a caregiver) may quickly drain the mobile computing device's battery. Thus, there is a need in the art to be able to communicate with wireless computing devices used to monitor persons-of-interest at any time, without draining their batteries.

SUMMARY OF THE INVENTION

The present disclosure is directed to inventive methods and apparatus for remotely initiating tasks on idle wireless computing devices. For example, a wireless computing device may be carried (e.g., operated, worn, etc.) by a person such as a patient that is to be monitored. In some situations, such as when the wireless device is used to monitor an elderly or otherwise at-risk patient, it may be important that the wireless device be able to receive commands at any time. But, as noted above, to operate the wireless device in an active state in which it is constantly connected to the one or more networks would quickly drain its battery. Accordingly, the wireless device may be idle but reachable over one or more networks, particularly a cellular network. Commands may be wirelessly transmitted to the wireless device, e.g., in short form, so that the wireless device can receive them even when in idle mode. For example, in embodiments where the wireless device is user equipment, commands may be transmitted to the wireless device using control plane signaling (e.g., an incoming telephone call). The wireless device may be configured to transition from an idle state to an active state and perform various tasks in response to such commands. For example, the wireless device may provide various data points pertaining to the person-of-interest's context (e.g., location, vital signs, etc.) on demand.

Generally, in one aspect, a wireless computing device for monitoring a person may include: a processor; one or more sensors operably coupled with the processor; and one or more radio antennas operably coupled with the processor. The processor may be configured to (e.g., by executing instructions in memory): transition the wireless computing device between at least an idle state in which the wireless computing device consumes a first amount of power and an active state in which the wireless computing device consumes a second amount of power that is greater than the first amount of power; receive, from a remote computing device via the one or more radio antennas while the wireless computing device is in the idle state, a request for one or more data points pertaining to a context of the person, wherein the request for one or more data points is received using control plane signaling; obtain one or more sensor signals from the one or more sensors; generate the requested one or more data points based on the one or more sensor signals; and provide, to the remote computing device via the one or more radio antennas, the requested one or more data points.

In various embodiments, the one or more sensors may include a heart rate sensor, and the requested one or more data points may include a pulse rate of the person. In various embodiments, the one or more sensors may include a position coordinate sensor, and the requested one or more data points may include a position coordinate of the person. In various embodiments, the control plane signaling may include Wi-Fi control plane signaling. In various embodiments, the control plane signaling may include radio resource control signaling. In various versions, the idle state of the wireless computing device may be IDLE, CELL_PCH, or URA_PCH.

In various embodiments, the request may be received via a first of the one or more antennas using a first wireless technology. The processor may be further configured to provide, to the remote computing device via a second of the one or more radio antennas using a second wireless technology that uses less power than the first wireless technology, the requested one or more data points.

In various embodiments, the request for one or more data points may be received as an incoming telephone call. In various versions, the controller may be configured to identify the request for one or more data points based on a telephone number associated with the incoming telephone call. In various versions, the wireless computing device may be a personal emergency response system or a smart watch. In various embodiments, the processor may be further configured to transition the wireless computing device from the idle state to the active state to perform one or more of the obtain, generate, and provide operations.

In another aspect, a method of monitoring a patient comprises transitioning a wireless computing device carried by the patient from an active state in which the wireless computing device consumes a first amount of power to an idle state in which the wireless computing device consumes a second amount of power, wherein the first amount of power is greater than the second amount of power, receiving, at the wireless computing device while the wireless computing device is in the idle state, wireless control plane signaling that includes a request for one or more data points pertaining to a context of the patient, obtaining, from one or more sensors associated with the wireless computing device, one or more sensor signals, and generating the requested one or more data points based on the one or more sensor signals.

In various embodiments, the method may further comprise determining that the requested one or more data points satisfy a criteria, and transmitting, by the wireless computing device to a remote computing device in response to the determining, the requested one or more data points to a remote computing device. In various embodiments, the wireless transmission may comprise an incoming telephone call.

In another aspect, a computing system is configured to provide a user interface, receive, at the user interface, a command to obtain one or more data points pertaining to a context of a person bearing user equipment, cause wireless transmission of a request for the one or more data points to the user equipment using control plane signaling, receive, directly or indirectly from the user equipment, data indicative of one or more sensor signals produced by one or more sensors associated with the user equipment.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

Various wireless computing devices may be equipped with a variety of sensors that enable the devices to be used to remotely monitor various attributes of persons-of-interest in various ways. However, maintaining network connections with such devices may quickly drain their batteries. Thus, there is a need in the art to be able to communicate with wireless computing devices used to monitor persons-of-interest at any time, without draining their batteries. More generally, Applicants have recognized and appreciated that it would be beneficial to remotely initiate tasks at mobile computing devices while those mobile computing tasks are in states that consume as little battery power as possible. In view of the foregoing, various embodiments and implementations of the present invention are directed to remote initiation of tasks on idle wireless computing devices.

Figure 1:
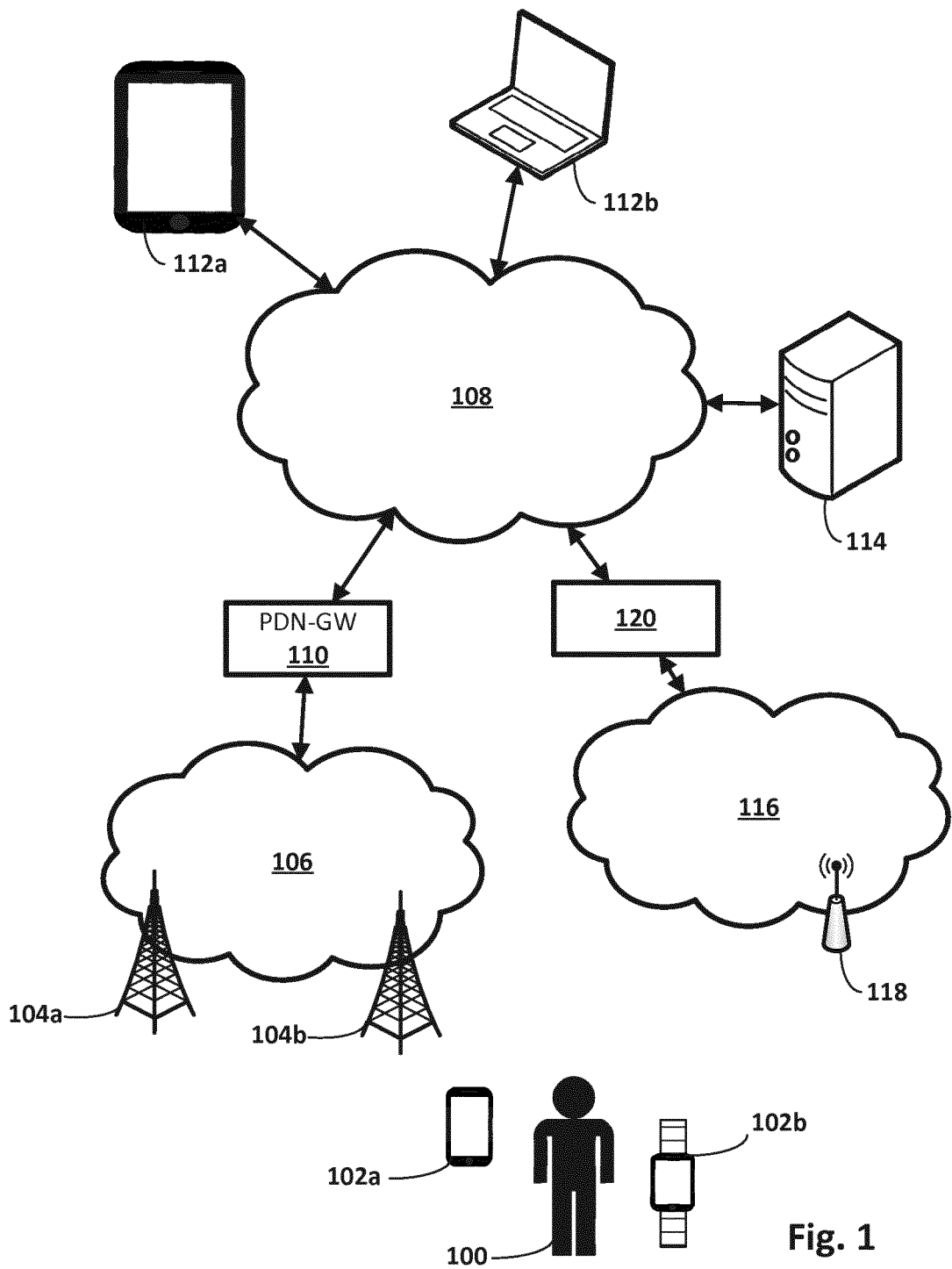
FIG. 1 schematically illustrates an example environment in which disclosed techniques may be employed, in accordance with various embodiments.

Referring to FIG. 1, a person-of-interest 100 may carry (e.g., operate, wear, etc.) one or more mobile computing devices 102, such as a smart phone 102a and/or a smart watch 102b. Mobile computing devices 102 may come in other portable forms as well, such as smart glasses, health monitoring devices (e.g., fitness trackers carried in a pocket), PERS, and so forth. Person-of-interest 100 may be any individual for which one or more attributes of the individual's context—location, vital signs, etc.—are of interest to others. For example, person-of-interest 100 may be an at-risk patient, such as an elderly person suffering from various conditions (e.g., dementia), or a patient at a mental health facility. As another example, person-of-interest 100 may be an inmate at a correctional facility, a parolee that is not permitted to leave a particular area, or any other person or persons who is/are subject to some sort of surveillance or monitoring for any number of reasons (e.g., a criminal suspect, repeat offender, travelling in dangerous area, member of expedition or fighting unit, athlete, race car driver, etc.).

Mobile computing devices 102 such as smart phone 102a and smart watch 102b may be equipped with various sensors (not depicted in FIG. 1, see FIG. 2) that may be operable to sense various stimuli and provide responsive signals. These signals may be indicative of various attributes of a context of person-of-interest 100 that are of interest to others. For example, a mobile computing device 102 may include a position coordinate sensor, such as a global position system ("GPS") sensor, a triangulation-based sensor (e.g., Wi-Fi triangulation), or a sensor to detect when person-of-interest has entered or exited a so-called "geofence." Additionally or alternatively, mobile computing device 102 may include various vital sign sensors, such as heart rate monitors, glucose sensors, blood pressure sensors, and so forth. Signals produced by one or more of these sensors may be indicative of data points pertaining to a context of person-of-interest 100 that are useful to others for various reasons. For example, a position coordinate of person-of-interest 100 may be of interest to law enforcement and/or to a caregiver. A heart rate of person-of-interest 100 may be of interest to medical personnel.

Mobile communication devices 102 may be configured to provide data indicative of these sensor signals to remote computing devices such as 112a and 112b in FIG. 1 that are operated by persons (e.g., caregivers, law enforcement) interested in this data. Mobile communication devices 102 may provide this data to remote computing devices 112 over one or more computing networks. For example, in FIG. 1, smart phone 102a and smart watch 102b may be in wireless range of one or more cell phone towers (in some instances, EnodeB's, or "eNB") 104a or 104b. Cell phone towers 104a-b may provide an interface to a cellular wireless network 106, which may be, for instance, an evolved packet core ("EPC"). Cellular wireless network 106 may be in communication with one or more wide area computing networks ("WAN") 108, such as the Internet, via various interface devices 110, such as a packet data network gateway, or "PDN-GW." Remote computing devices 112a-b likewise may be connected to WAN 108, directly or indirectly, using wireless or wired connections. In some embodiments, remote computing devices 112a-b may be connected to WAN 108 via one or more cellular networks (e.g., 106, or another cellular network). Of course, the configuration depicted in FIG. 1 is not meant to be limiting, and other configurations are possible.

A remote task initiation control server ("RTICS") 114 is also depicted in FIG. 1. RTICS 114 may include one or more computing systems connected by one or more networks (not depicted, e.g., a server farm) that operate in cooperation to manage how mobile computing devices such as smart phone 102a or smart watch 102b are remotely controlled to various degrees by remote computing devices, such as 112a and 112b. In various embodiments, RTICS 114 may manage various aspects of connections between wireless computing devices 102 and remote computing devices 112. For example, RTICS 114 may maintain a database of identifiers for mobile computing devices 102, such as telephone numbers. In some embodiments, RTICS 114 may maintain in the same database or in a different database a lookup table of tasks that may be remotely initiated at individual mobile computing devices 102 (which may depend on their capabilities), as well as specific commands that may be sent to mobile computing devices 102 in order to initiate those tasks. For example, in some embodiments, a task may be initiated at a mobile computing device 102 by placing a telephone call to mobile computing device 102 with a particular caller ID that matches a desired task.

Also depicted in FIG. 1 is an optional local area network ("LAN") 116 provided by a wireless access point 118. In various embodiments, LAN 116 may be provided in an environment in which person-of-interest 100 resides or spends time, such as a home, a workplace, a correctional facility, a hospital room, a psychiatric ward, a nursing home, and so forth. LAN 116 may be used for various purposes. Suppose an idle mobile computing device 102 is "awoken," e.g., in response to a command from a remote computing device 112 received over cellular network 106, to perform a task (e.g., provide data indicative of a vital sign or location of person-of-interest 100). In some embodiments, mobile computing device 102 may provide the requested data to remote computing device 112 through LAN 116, in addition to or instead of through cellular network 106. Additionally or alternatively, LAN 116 may be used to monitor a location of user-of-interest 100, e.g., by operating a geofence that detects when mobile computing device 102 loses Wi-Fi connection with access point 118.

Figure 2:
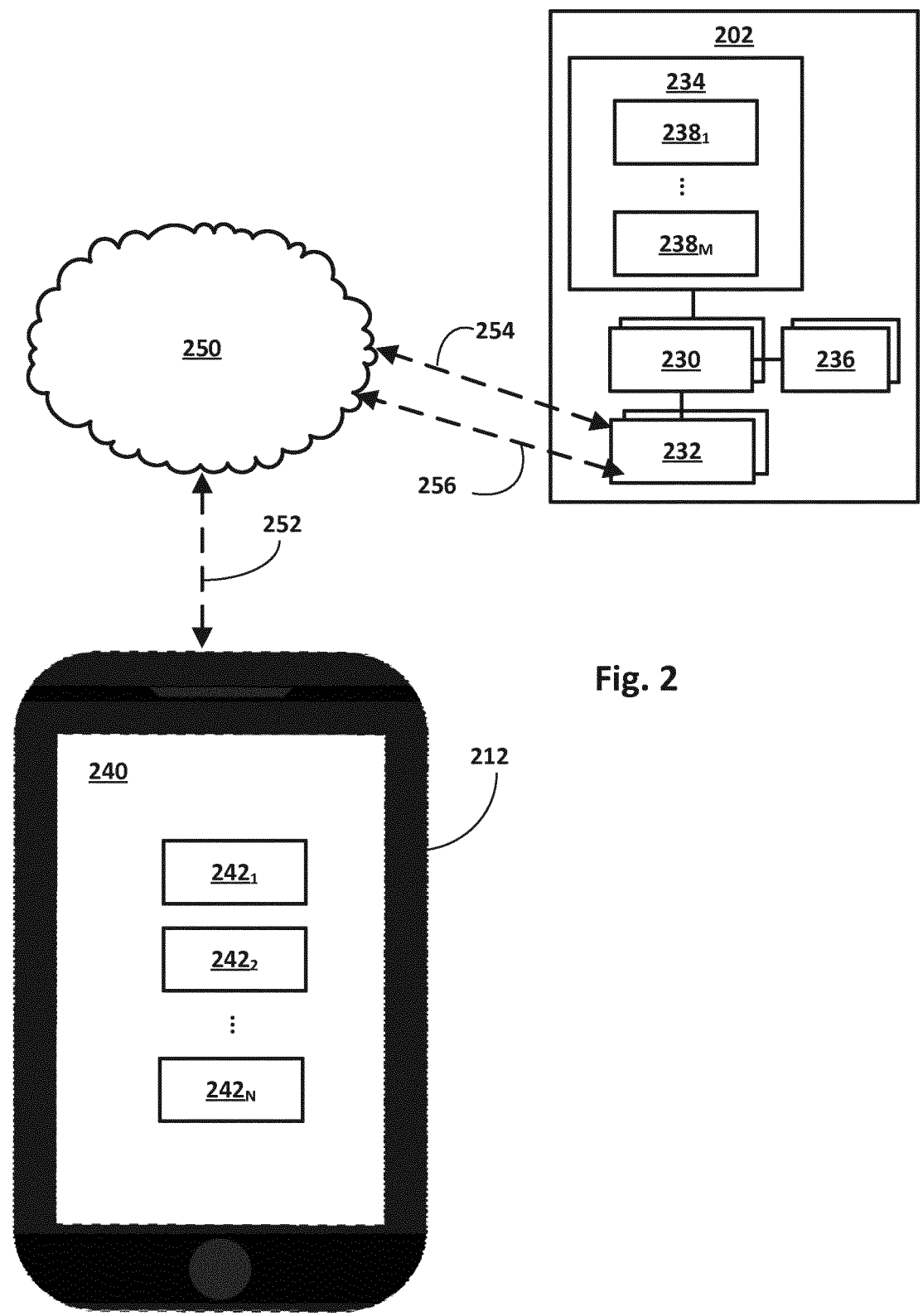
FIG. 2 schematically illustrates, in more detail than FIG. 1, an example of how a mobile computing device configured with selected aspects of the present disclosure may be remotely controlled, in accordance with various embodiments.

FIG. 2 schematically depicts in more detail than FIG. 1 various components of a mobile computing device 202 configured with selected aspects of the present disclosure, as well as how mobile computing device 202 interacts with a remote computing device 212. For the sakes of brevity and simplicity, in FIG. 2, the various networks depicted in Fig. 1 (e.g., 106, 108, 116) are represented by the single network 250. In this non-limiting embodiment, mobile computing device 202 may include one or more processors 230 operably coupled with one or more radio antennas 232, memory 234, and one or more sensors 236. Radio antennas 232 may come in various forms to communication using various technologies such as Wi-Fi, cellular (e.g., 2G, 3G, 4G, future variants thereof, etc.), BlueTooth, and so forth. For example, many smart phones or smart watches include at least three antennas: one for cellular communication, one for Wi-Fi communication, and one for Bluetooth. Memory 234 may come in various forms, such as RAM, DRAM, flash, ROM, and so forth. One or more sensors 236 may come in various forms as well, including but not limited to position coordinate sensors (e.g., GPS, Wi-Fi triangulation), accelerometers, gyroscopes, vital sign sensors (e.g., heart rate, blood pressure, blood glucose), thermometers, light sensors, cameras, microphones, barometers, pedometers, and so forth.

In FIG. 2, mobile computing device 202 may be connected to network 250 as indicated at 252 using various technologies, such as Wi-Fi, Ethernet, cellular, and so forth. Mobile computing device 202 may be connected to network 250 in some embodiments using a cellular connection that includes a control plane 254 and a data plane 256 (sometimes referred to as a "user plane"). Control plane 254 may be used to exchange various control signals with mobile computing device 202, e.g., to establish a connection with mobile computing device 202. Depending on the wireless technology employed and/or available while mobile computing device 202 is idle (explained further below), control plane 254 may be implemented in various ways, including but not limited to using radio resource control ("RRC") signals, Wi-Fi control plane signals, proxy mobile IPv6 ("PMIP") control plane signaling, non-access stratum ("NAS") signals, and so forth. Data plane 256 may be used to exchange data with mobile computing device 202 once a connection is established.

In some embodiments, mobile computing device 202 may be transitioned between various states in which it consumes various amounts of power. For example, in an idle mode, one or more radio antennas 232 of mobile computing device 202 may be limited in their functionality, e.g., with no transport channels allocated, etc., and may be limited to performing low power tasks such as listening for pages. In such a state, mobile computing device 202 may consume a minimal amount of power. Mobile computing device 202 may be transitioned from its idle mode to various active states in response to various events, such as receipt of a page (e.g., for an incoming telephone call), receipt of a notification using control plane signaling, and so forth. In an active state, one or more antennas 232, particularly a cellular antenna, may be operational, and mobile computing device 202 may have allocated one or more transport channels that it can use to send and/or receive data.

In some embodiments in which mobile computing device 202 operates using universal mobile telecommunications system ("UMTS") cellular technology, mobile computing device 202 may be considered to be in an active state when it is in the CELL_DCH (dedicated channel) mode or the CELL_FACH (forwarding address channel) mode, and in the idle state while in the IDLE or CELL_PCH (passive channel) modes. In some embodiments in which mobile computing device 202 operates using Long Term Evolution ("LTE") cellular technology (e.g., 4G LTE), mobile computing device 202 may be considered to be in an active state when it is in the RRC_CONNECTED state, and in an idle state when it is in the RRC_IDLE state. Of course, these are just non-limiting examples of idle and active modes or states.

In various embodiments, remote computing device 212 may be operated to remotely initiate a task on mobile computing device 202, even when mobile computing device 202 is in an idle mode. For example, remote computing device 212 may be configured to receive, at a user interface 240 (e.g., a graphical user interface rendered on a touch screen), a command to obtain one or more data points pertaining to a context of a person (e.g., person-of-interest 100) bearing user equipment (e.g., 102a, 102b, 202). For example, in some embodiments, user interface 240 of remote computing device 212 may include a plurality of operable elements, 2421-242N, which may be operable to initiate one or more of a plurality of tasks or routines 2381-238M stored in memory 234 of mobile computing device 202. Remote computing device 212 may then cause wireless transmission of a request for the one or more data points to mobile computing device 202 using control plane signaling (e.g., over control plane 254). Remote computing device 212 may receive, directly or indirectly from mobile computing device 202, data indicative of one or more sensor signals produced by one or more sensors (e.g., 236) associated with mobile computing device 202.

For its part, mobile computing device 202 may be configured to receive, from remote computing device 212 via the one or more radio antennas 232 while mobile computing device is in the idle state, the request for one or more data points pertaining to a context of the person (e.g., person-of-interest 100). Mobile computing device 202 may obtain one or more sensor signals from one or more sensors 236 and generate the requested one or more data points based on the one or more sensor signals. In some embodiments, mobile computing device 202 may transition from the idle state to the active state in order to obtain the sensor signals/generate the data points. Mobile computing device 202 may then provide, to remote computing device 212 using the same radio antenna 232 or a different radio antenna 232, the requested one or more data points.

Figure 3:
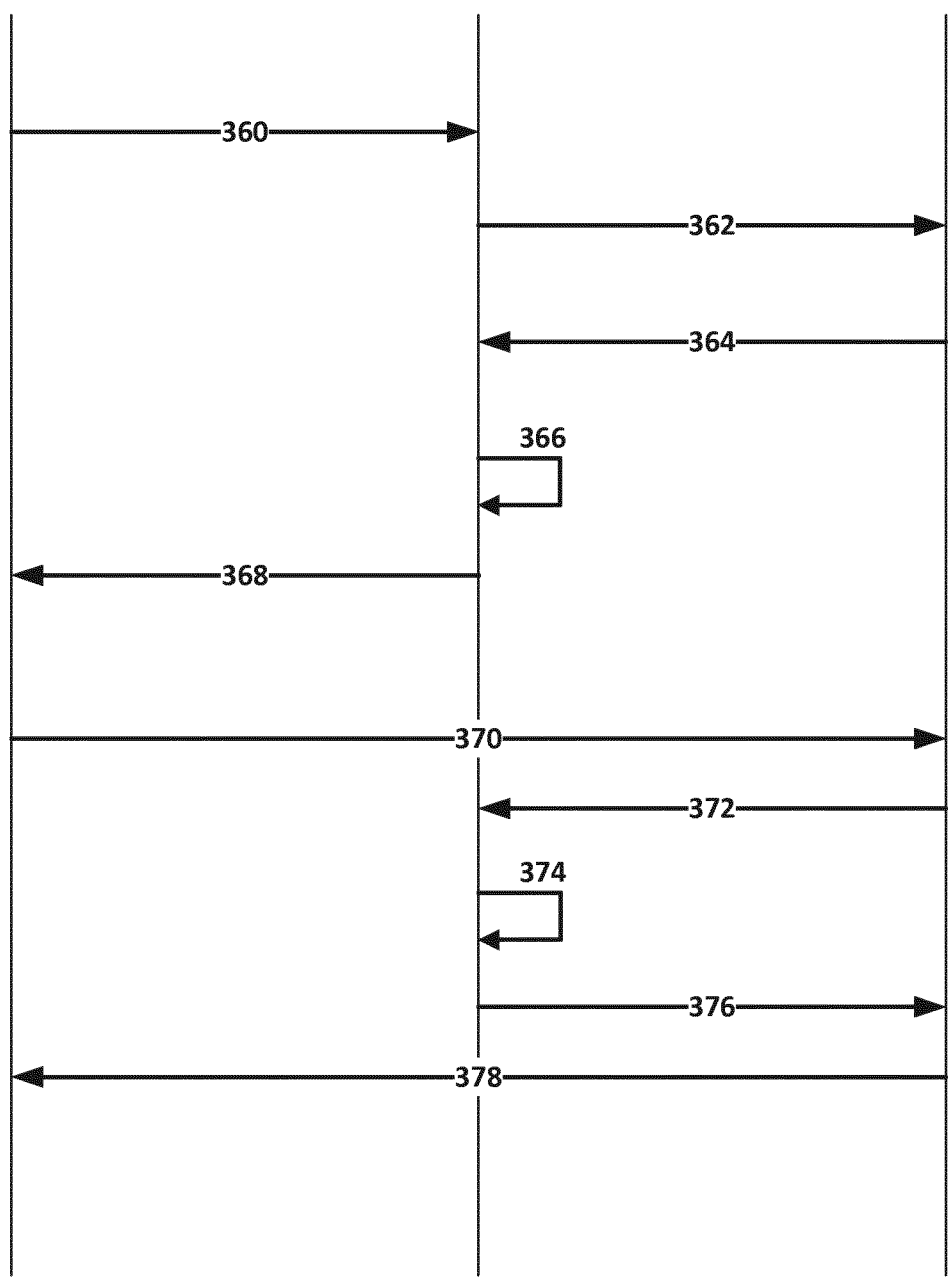
FIG. 3 depicts example communication exchanges that may occur between a mobile computing device and one or more remote computing devices, in accordance with various embodiments.

FIG. 3 depicts examples of how a remote computing device 312 may remotely initiate tasks at a mobile computing device 302 carried by a person-of-interest, in accordance with various embodiments. A first exchange depicted at 360-368 begins with remote computing device 312 initiating contact with mobile computing device 302 at 360 in a manner that mobile computing device 302 can detect while in an idle mode For example, remote computing device 312 may initiate a telephone call to mobile computing device 302 at 360. As part of initiating a telephone call, remote computing device 312 may provide a telephone number and/or caller ID to be received at mobile computing device 302. In some embodiments, a telephone number and/or caller ID provided by remote computing device 312 may be linked via a unique identifier, such as an International Mobile Station Equipment Identity, or "IMIE."

At 362, mobile computing device 302 may transition from an idle mode to an active mode to transmit a request to RTICS 314 to match the received caller ID to a particular task. In other embodiments, mobile computing device 302 may match the caller ID to a task stored in its own memory, without needing to reach out to RTICS 314. At 364, RTICS may return data indicative of a matched task to mobile computing device 302. At 366, mobile computing device 302 may perform the requested task. For example, mobile computing device 302 may obtain one or more sensor readings, such as a position coordinate of person-of-interest 100, or a vital sign. At 368, mobile computing device 302 may provide the requested data to remote computing device 312. The operator of remote computing device 312 may then take appropriate action, such as deploying personnel to track down an elderly person-of-interest who has wandered away.

Another example data exchange (which does not necessarily have to occur after the first example exchange, and is illustrated below the first exchange for convenience only) begins at 370 with remote computing device 312 transmitting a request to RTICS 314 for one or more data points pertaining to a context of a person-of-interest. The communication at 370 may be issued using various network technologies, and is not necessarily limited to cellular since RTICS 314 is likely not battery powered, and thus may not be in idle mode. At 372, RTICS 314 may transmit a request for the one or more data points requested by remote computing device 312 to mobile computing device 302, e.g., by initiating a cellular telephone call with to mobile computing device 302. At 374, mobile computing device 302 may perform whatever task necessary to obtain the requested data points. For example, mobile computing device 302 may obtain one or more sensor readings, such as a position coordinate of person-of-interest 100, or a vital sign. At 376, mobile computing device 302 may provide the requested data to RTICS 314, e.g., using a cellular connection or by using another networking technology. At 378, RTICS 314 may provide data indicative of the requested one or more data points to remote computing device 312, e.g., using the same or different networks as were used at 370.

Figure 4:
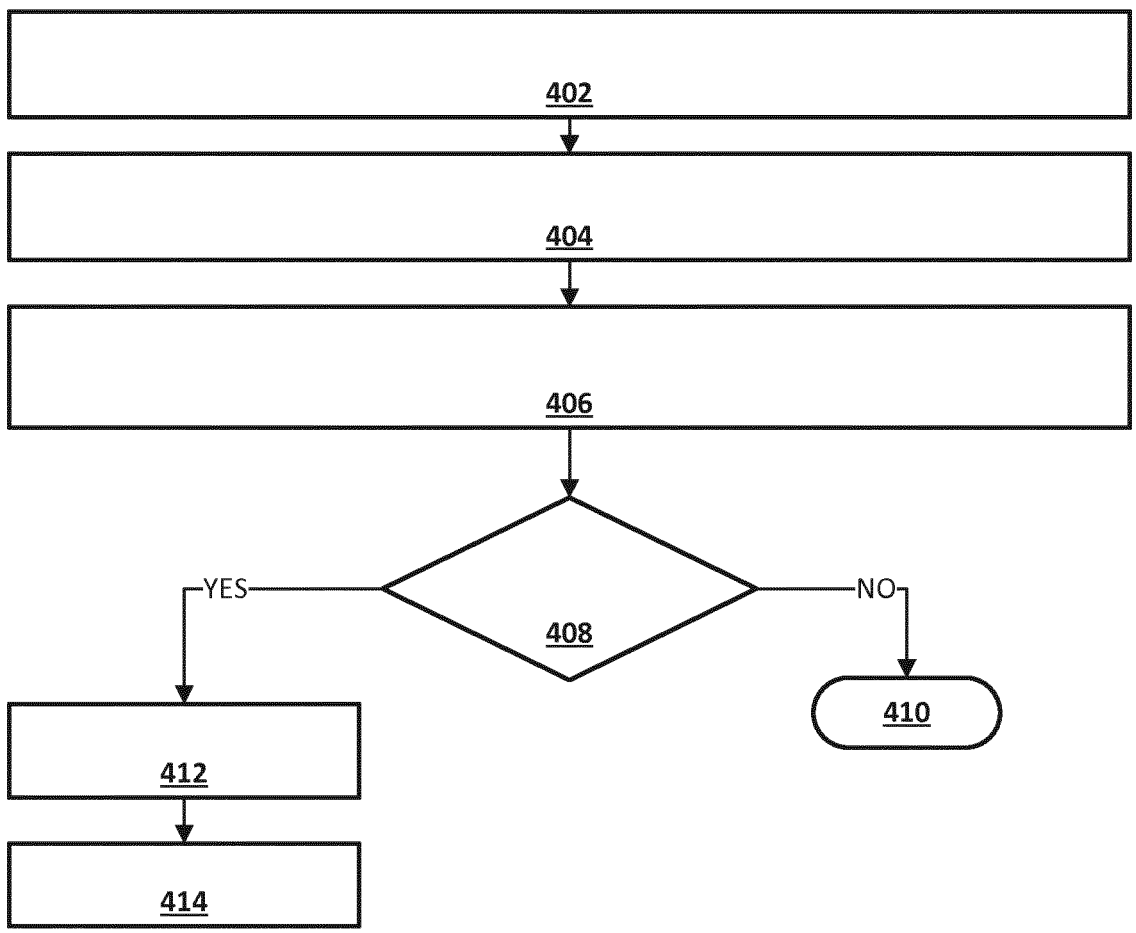
FIGS. 4 and 5 depict example methods that may be implemented in accordance with various embodiments.

FIG. 4 depicts an example method 400 that may be implemented by a mobile computing device (e.g., 102a, 102b, 202, 302) carried by a person-of-interest (e.g., 100), in accordance with various embodiments. While certain operations are depicted in a particular order, this is not meant to be limiting. In various embodiments, one or more operations may be added, omitted, and/or reordered.

At block 402, the mobile computing device may transition from an active state (e.g., CELL_FACH, CELL_DCH, RRC_CONNECTED) in which the wireless computing device consumes a first amount of power to an idle state (e.g., CELL_PCH, IDLE, RRC_IDLE) in which the wireless computing device consumes a second amount of power, wherein the first amount of power is greater than the second amount of power. This may occur, for instance, because the mobile computing device has been inactive for a predetermined amount of time, and/or has not sent or received any communications for a predetermined amount of time.

At block 404, the mobile computing device may receive, e.g., at its cellular radio antenna while it is in the idle state, a wireless transmission that includes a request for one or more data points pertaining to a context of the person-of-interest that bears the mobile computing device. As noted above, this request may be received from various sources, such as directly from a remote computing device (e.g., 112, 212, 312) operated by someone monitoring the person-of-interest, or from an RTICS server (e.g., 114, 314). At block 406, the mobile computing device may obtain, from one or more sensors (e.g., 236) associated with the wireless computing device, one or more sensor signals, such as vital signs, location, etc. In some embodiments, the mobile computing device may transition from the idle mode to the active mode in order to obtain the sensor signals at block 406.

At optional block 408, the mobile computing device may determine whether the requested one or more data points satisfy a criteria. For example, if the sensor signal(s) indicate the person-of-interest is where they are supposed to be, a criterion that the person-of-interest has left an authorized area may not be satisfied. But, if the person-of-interest has left the authorized area, then the criterion may be satisfied. If the answer at block 408 is no, then method 400 may end at block 410. However, if the answer at 408 is yes, or if block 408 is omitted, at block 412, the mobile computing device may generate the requested one or more data points based on the one or more sensor signals.

In some embodiments, at block 414, the mobile computing device may transmit the requested one or more data points to a remote computing device (e.g., 112, 212, 312), e.g., using the communication channel as was used at block 404, or using a different communication channel. For example, where the request is received at block 404 via a first of one or more antennas (e.g., 232) using a first wireless technology, the requested one or more data may be provided to the remote computing device at block 414 through a second of the one or more radio antennas 232 using a second wireless technology. In some embodiments, the second antenna and/or wireless technology may use less power than the first wireless technology. Suppose the request is received at block 404 using cellular technology, which may be considered to consume relatively large amounts of power and/or to be unreliable. The requested one or more data points may be returned to the remote computing device at block 414 using a lower power and/or more reliable wireless technology/antenna, such as Wi-Fi or Bluetooth. In other instances, such as when the mobile computing device is simply used to track one or more parameters of a person-of-interest over a period of time (e.g., to track travel pattern, track vital signs, etc.), then the mobile computing device may not necessarily send the requested data back to the remote computing device at each measurement, but may instead simply store an indication of the measurement for future analysis.

Figure 5:
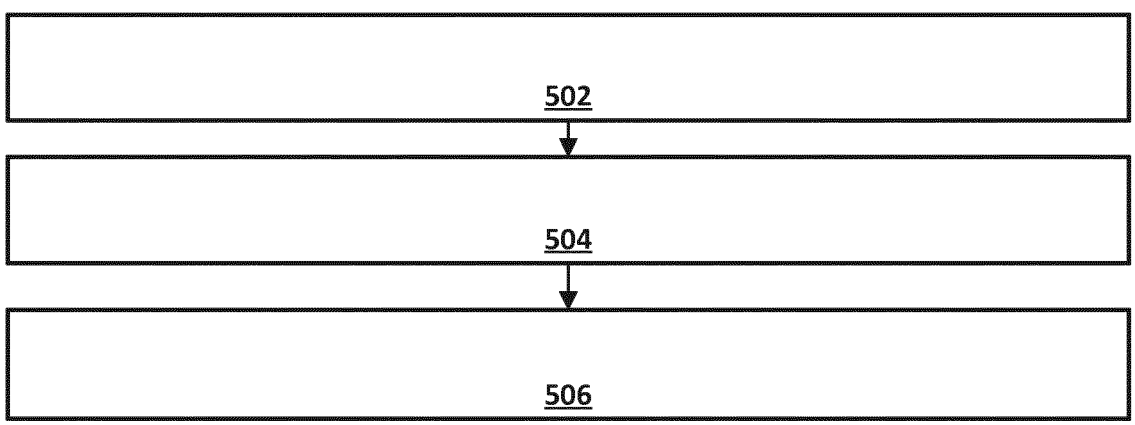

FIG. 5 depicts an example method 500 that may be implemented by a remote computing device computing device (e.g., 112, 212, 312) operated by someone who is monitoring a person-of-interest (e.g., 100), in accordance with various embodiments. While certain operations are depicted in a particular order, this is not meant to be limiting. In various embodiments, one or more operations may be added, omitted, and/or reordered.

At block 502, the remote computing device may receive, at a user interface (e.g., 240), a command to obtain one or more data points pertaining to a context of a person bearing user equipment (e.g., a mobile device such as 102, 202, 302). At block 504, the remote computing device may cause wireless transmission of a request for the one or more data points to the user equipment using control plane signaling. At block 506, the remote computing device may receive, directly or indirectly from the user equipment, data indicative of one or more sensor signals produced by one or more sensors associated with the user equipment.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

The invention claimed is:

1. A wireless computing device for monitoring a person, comprising:
   a processor;
   one or more sensors operably coupled with the processor; and
   one or more radio antennas operably coupled with the processor, wherein the processor is configured to:
      transition the wireless computing device between at least an idle state in which the wireless computing device consumes a first amount of power and an active state in which the wireless computing device consumes a second amount of power that is greater than the first amount of power;
      receive, from a remote computing device via the one or more radio antennas using a first wireless technology while the wireless computing device is in the idle state, a request for one or more data points pertaining to a context of the person, wherein the request for one or more data points is received using control plane signaling as an incoming telephone call;
      obtain one or more sensor signals from the one or more sensors;
      generate the requested one or more data points based on the one or more sensor signals; and
      provide, to the remote computing device via the one or more radio antennas using a second wireless technology, the requested one or more data points, wherein the second wireless technology uses less power than the first wireless technology.

2. The wireless computing device of claim 1, wherein the one or more sensors comprise:
   a heart rate sensor, and the requested one or more data points include a pulse rate of the person.

3. The wireless computing device of claim 1, wherein the one or more sensors comprise:
   a position coordinate sensor, and the requested one or more data points include a position coordinate of the person.

4. The wireless computing device of claim 1, wherein the control plane signaling further comprises Wi-Fi control plane signaling.

5. The wireless computing device of claim 1, wherein the control plane signaling further comprises radio resource control signaling.

6. The wireless computing device of claim 5, wherein the idle state of the wireless computing device further comprises IDLE, CELL_PCH, or URA_PCH.

7. The wireless computing device of claim 1, wherein the request is received via a first of the one or more antennas using the first wireless technology, and the processor is further configured to provide, to the remote computing device via a second of the one or more radio antennas using the second wireless technology the requested one or more data points.

8. The wireless computing device of claim 1, wherein the controller is further configured to identify the request for one or more data points based on a telephone number associated with the incoming telephone call.

9. The wireless computing device of claim 1, wherein the wireless computing device further comprises:
   a personal emergency response system or a smart watch.

10. The wireless computing device of claim 1, wherein the processor is further configured to transition the wireless computing device from the idle state to the active state to perform one or more of the obtain, generate, and provide operations.

11. A method of monitoring a patient, comprising:
   transitioning a wireless computing device carried by the patient from an active state in which the wireless computing device consumes a first amount of power to an idle state in which the wireless computing device consumes a second amount of power, wherein the first amount of power is greater than the second amount of power;
   receiving, at the wireless computing device using a first wireless technology while the wireless computing device is in the idle state, wireless control plane signaling that includes a request for one or more data points pertaining to a context of the patient, wherein the request is received as an incoming telephone call;
   obtaining, from one or more sensors associated with the wireless computing device, one or more sensor signals;
   generating the requested one or more data points based on the one or more sensor signals; and
   providing, to a remote computing device via one or more radio antennas using a second wireless technology, the generated one or more data points, wherein the second wireless technology uses less power than the first wireless technology.

12. The method of claim 11, further comprising:
   determining that the requested one or more data points satisfy a criterion; and
   transmitting, by the wireless computing device to a remote computing device in response to the determining, the requested one or more data points to a remote computing device.

13. A computing system configured to:
   provide a user interface;
   receive, at the user interface, a command to obtain one or more data points pertaining to a context of a person bearing user equipment;
   cause wireless transmission of a request for the one or more data points to the user equipment using control plane signaling, wherein the wireless transmission comprises an incoming telephone call;
   receive, using a first wireless technology, from the user equipment, data indicative of one or more sensor signals produced by one or more sensors associated with the user equipment; and
   providing, to a remote computing device via one or more radio antennas using a second wireless technology, one or more data points generated based on the one or more sensor signals, wherein the second wireless technology uses less power than the first wireless technology.

* * * * *